United States Patent
Jimenez et al.

(10) Patent No.: US 10,241,086 B2
(45) Date of Patent: Mar. 26, 2019

(54) VALIDATION OF CASED-HOLE ACOUSTIC TOOLS

(71) Applicant: Halliburton Energy Services, Inc., Houston, TX (US)

(72) Inventors: Walmy Cuello Jimenez, Duncan, OK (US); Xueyu Pang, Houston, TX (US); Paul Jones, Humble, TX (US); Robert Eric Epstein, Spring, TX (US); Zachary Edward Gordon, Conroe, TX (US); Batakrishna Mandal, Fort Bend, TX (US); Tatiana Gilstrap, The Woodlands, TX (US)

(73) Assignee: Halliburton Energy Services, Inc., Houston, TX (US)

(*) Notice: Subject to any disclaimer, the term of this patent is extended or adjusted under 35 U.S.C. 154(b) by 311 days.

(21) Appl. No.: 15/028,761

(22) PCT Filed: Nov. 12, 2013

(86) PCT No.: PCT/US2013/069719
§ 371 (c)(1),
(2) Date: Apr. 12, 2016

(87) PCT Pub. No.: WO2015/072976
PCT Pub. Date: May 21, 2015

(65) Prior Publication Data
US 2016/0238562 A1 Aug. 18, 2016

(51) Int. Cl.
*G01N 29/09* (2006.01)
*E21B 47/00* (2012.01)
*E21B 47/10* (2012.01)
*G01N 17/00* (2006.01)
*G01V 1/40* (2006.01)
*E21B 33/14* (2006.01)

(52) U.S. Cl.
CPC ......... *G01N 29/09* (2013.01); *E21B 47/0005* (2013.01); *E21B 47/101* (2013.01);
(Continued)

(58) Field of Classification Search
CPC .................. G01N 29/09; G01N 17/00; G01N 2291/0232; G01V 1/40; E21B 47/0005; E21B 47/101; E21B 33/14
See application file for complete search history.

(56) References Cited

U.S. PATENT DOCUMENTS

| 4,809,236 A | 2/1989 | Hsu et al. |
| 5,036,496 A | 7/1991 | Rutledge |
(Continued)

FOREIGN PATENT DOCUMENTS

| EP | 2513674 A2 | 10/2012 |
| WO | WO2011075280 | 6/2011 |

OTHER PUBLICATIONS

Foianini et al., Cement Evaluation Behind Thick-Walled Casing with Advanced Ultrasonic Pulse-Echo Technology: Pushing the Limit, Manuscript, 54th SPWLA Symposium, Jun. 2013, 6 pages.
(Continued)

*Primary Examiner* — Xin Y Zhong
(74) *Attorney, Agent, or Firm* — John W. Wustenberg; Parker Justiss, P.C.

(57) ABSTRACT

In some implementations, a method for validating an acoustic bond-log tool includes having a test fixture including a wellbore casing emulating tubing. An outer tubing emulates a well formation and forms a perimeter of an annulus surrounding the wellbore casing emulating tubing. The wellbore casing tubing is configured with a stepped outer surface emulating different wellbore casing sidewall thicknesses. A dividing structure is coupled in the axial direction to the outer surface of the wellbore casing emulating tubing and to the inner surface of the outer tubing to radially subdivide the annulus into a plurality of hermetically sealable sample sections. Each sample section contains a sample of a material having a known acoustic impedance. The acoustic bond-log tool is validated by comparing a bond-log
(Continued)

tool measurement of the acoustic impedance of each sample in a particular sample section to the known acoustic impedance of the sample.

23 Claims, 4 Drawing Sheets

(52) U.S. Cl.
CPC .............. *G01N 17/00* (2013.01); *E21B 33/14* (2013.01); *G01N 2291/0232* (2013.01); *G01V 1/40* (2013.01)

(56) References Cited

U.S. PATENT DOCUMENTS

| 5,197,038 | A | 3/1993 | Chang et al. |
| 5,216,638 | A | 6/1993 | Wright |
| 5,571,951 | A | 11/1996 | Jamth |
| 5,763,773 | A | 6/1998 | Birchak et al. |
| 6,208,585 | B1 | 3/2001 | Stroud |
| 2010/0246325 | A1* | 9/2010 | Egerev .................... G01V 1/44 367/29 |
| 2013/0114377 | A1 | 5/2013 | Frisch |

OTHER PUBLICATIONS

Foianini et al., Cement Evaluation Behind Thick-Walled Casing with Advanced Ultrasonic Pulse-Echo Technology: Pushing the Limit, Manuscript, 54th SPWLA Symposium, Powerpoint Presentation, Jun. 2013, 12 pages.

PCT International Search Report and Written Opinion of the International Searching Authority, PCT/US2013/069719, dated Aug. 14, 2014, 10 pages.

* cited by examiner

VALIDATION OF CASED-HOLE ACOUSTIC TOOLS

CROSS-REFERENCE TO RELATED APPLICATIONS

This application is a U.S. National Phase Application under 35 U.S.C. § 371 and claims the benefit of priority to International Application Serial No. PCT/US2013/069719, filed on Nov. 12, 2013, the contents of which are hereby incorporated by reference.

BACKGROUND

The specification relates to a test fixture for validating an acoustic bond-log tool. Cement and casing operations comprise an integral part of well construction. Cement is placed downhole to support and protect the casing string, and to provide effective zonal isolation during the entire life of the well, thus, supplying a mechanical barricade that isolates the different zones in the well. If zonal isolation is not ensured, many issues can arise including sustainable casing pressure, flows between reservoirs, undesirable flow behind a casing, etc. These issues may lead not only to severe operational difficulties but also to the loss of the well. Cased-hole ultrasonic (acoustic bond-log) tools play a key role in determining whether well repair and the economic cost associated with it is necessary or not. Attempting to validate and/or calibrate an acoustic bond-log tool using an actual well is difficult and generally cost-prohibitive or not possible, in addition to the fact that the validation and/or calibration points are limited to the cement system(s) in that actual wellbore. Therefore, certainty of accuracy and an overall efficiency of leveraging acoustic bond-log tools for cement testing is reduced.

DESCRIPTION OF DRAWINGS

Like reference numbers and designations in the various drawings indicate like elements.

DETAILED DESCRIPTION

The specification relates to a test fixture for validating an acoustic bond-log tool. The details of one or more implementations of the subject matter of this specification are set forth in the accompanying drawings and the description below. Other features, aspects, and advantages of the subject matter will become apparent from the description, the drawings, and the claims.

Cement and casing operations comprises an integral part of well construction as cement supports and protect the casing string, and provides effective long term zonal isolation supplying a mechanical barricade that isolates the different formations in the wellbore. Cased-hole ultrasonic (acoustic bond-log) tools (ABTs) play a key role in cement evaluation. Therefore, there is a great need for developing an optimum validation system for the ABTs employed during casing and cement evaluation its wells.

The test fixture can emulate casing-in-hole or casing-in-casing well configurations and includes a wide range of cement-based or other media with different acoustic properties. In addition, the performance of the ABT under the presence of water, various muds, drilling, and/or displacement fluids can also be studied. Different temperature and pressure conditions can also be emulated within the text fixture. Many factors can affect the values/accuracy of ABTs, including factors associated with running the ABT, factors controlled during cementing operations, or factors intrinsic to a wellbore or formation. The described test fixture and method can evaluate the performance of ABTs with a variety of factors that can be introduced into emulated well configurations. For example, the test fixture and method can be used to evaluate ABT accuracy at identifying factors such as microannulus, eccentralization, logging tool centralization, light weight and foam cements, cement setting time, fast formations, and/or other factors.

The test fixture and method will also allow for determining the operational performance, accuracy, and reliability of ABTs by subjecting them to a wide range of casing sizes. Moreover, the accuracy of the ABTs at detecting newly emerging zonal isolation materials, such as various resins, can also be determined. The test fixture and method can also be used to develop new algorithms for acoustic logging data interpretation.

Figure 1:
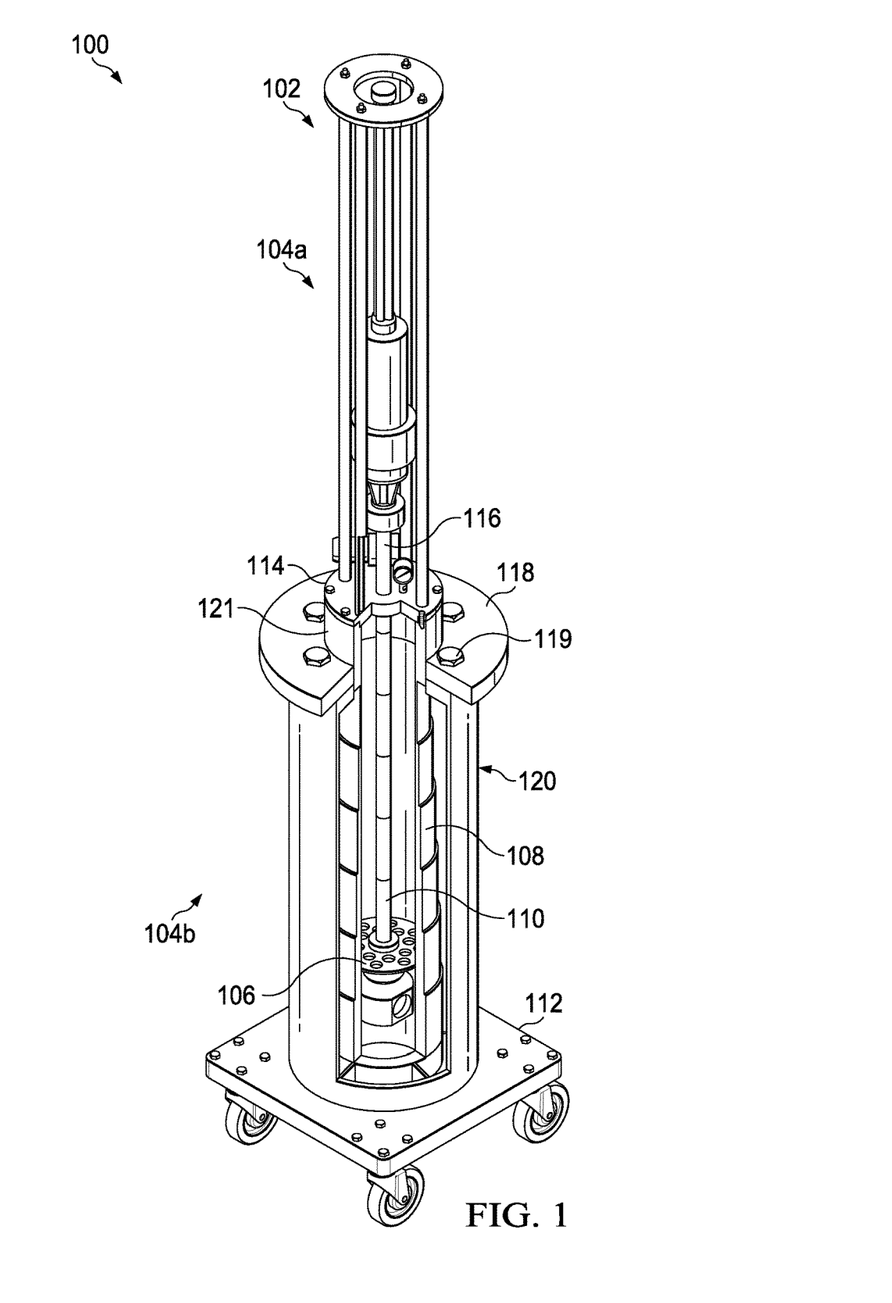
FIG. 1 is perspective cut-away view of an example test fixture for validating an acoustic bond-log tool according to an implementation.

FIG. 1 is cut-away view of 100 an example test fixture 102 for validating an ABT according to an implementation. The test fixture is made up of two primary sections: 1) a tool guide 104a and 2) a testing portion 104b. The tool guide 104a is used to guide the ABT 106 within a wellbore casing emulating tubing 108 configured with an internal bond-log tool receiving bore 110. The testing portion 104b is used for validating an ABT. Although the test fixture 102 is illustrated as configured with a wheeled mounting base 112, in other implementations, the test fixture 102 can be mounted to a non-moveable base or other support structure.

In some implementations, the internal bond-log tool receiving bore 110 has a uniform internal diameter in the axial direction allowing for differently sized ABTs to be evaluated while holding the internal bond-log tool receiving bore 110 internal diameter constant. In other implementations, the internal bond-log tool receiving bore 110 can have a varying internal diameter. For example, the internal diameter can taper from top to bottom or vary in some non-uniform graduation in the axial direction.

The exterior surface of the wellbore casing emulating tubing 108 is configured with an axially-stepped outer surface emulating different wellbore casing sidewall thicknesses. In some implementations, the axially-stepped outer surface can uniformly step in increasing/decreasing thickness traveling axially upward or downwards along the wellbore casing emulating tubing 108. In other implementations, the steps can vary in a non-uniform graduation in an axial direction. In some implementations, the wellbore casing emulating tubing 108 can radially be of a uniform thickness.

In some implementations, the wellbore casing emulating tubing 108 is configured to accept a wellbore tubing upper end module 114 that seals the internal bond-log tool receiving bore 110. In some implementations, the seal provided by the wellbore tubing upper end module 114 is hermetic. The wellbore tubing upper end module 114 is configured with a hole to permit a shaft 116 attached to the ABT 106 to be inserted into the internal bond-log tool receiving bore 110. The hole is configured with a sealing material to provide a seal around the shaft 116 in order to preserve the internal bond-log tool receiving bore 110 seal provided by the wellbore tubing upper end module 114.

In some implementations, the lower end of the wellbore casing emulating tubing 108 is sealed. For example the lower end can have been machined with a closed end or can be closed by attachment to another surface, such as the upper surface of the wheeled mounting base 112 or other base/support. Attachment can be, for example, by fasteners, welding, adhesives, and/or other attachments and can provide a hermetic seal.

The testing portion 104b is configured with art upper end module 118 coupled to an outer tubing 120. The outer tubing 120 emulates a well formation and forms a perimeter of an annulus surrounding the wellbore casing emulating tubing 108. In some implementations, the upper end module 118 can be attached to the outer tubing 120 using a fastener 119. Although fastener 119 is illustrated as a bolt, fasteners can include screws, clamps, latches, adhesives, and/or other fasteners permitting the removal of the upper end module 118 from the outer tubing 120. In some implementations, the upper end module 118 and the outer tubing 120 can be welded together. In these implementations, the upper end module 118 can be configured with one or more sealable holes to allow cement to be poured into the testing portion 104b. In some implementations, the sealable holes can be sealed with a fastener 119, such as a screw or a bolt. In some implementations, the lower surface of the upper end module 118 and/or the upper edge surface of the outer tubing 120 can provide a seal when the two surfaces are coupled. In some implementations, the provided seal can be hermetic. In some implementations, the outer tubing 120 can be made out of other materials with different properties and different thicknesses to emulate different formations.

In some implementations, the upper end module 118 surrounds an upper portion 121 of the wellbore casing emulating tubing 108 protruding above the upper surface of the upper end module 118. In other implementations, the upper surface of the wellbore tubing upper end module 114 can be flush or depressed in relation to the upper surface of the upper end module 118. In some implementations, the inner surface of the upper end module 118 and/or the outer surface of the upper portion 121 of the wellbore casing emulating tubing 108/wellbore tubing upper end module 114 can provide a seal when adjacently situated. In some implementations, the provided seal can be hermetic.

In some implementations, the lower end of the outer tubing 108 is sealed. For example the lower end of the outer tubing 108 can have been machined with a closed end or the lower end can be hermetically sealed by attachment to another surface, such as the upper surface of the wheeled mounting base 112 or other base/support.

In some implementations, the upper end module 118 can be configured with one or more ports (not illustrated) providing access through the upper end module 118 and into the annular space created between the outer tubing 120 and the wellbore casing emulating tubing 108. In some implementations, the upper surface of the well bore tubing upper end module 114 can be configured with one or more ports (not illustrated) providing access to the wellbore tubing. In some implementations, a port can be coupled to a pump (not illustrated) capable of producing wellbore pressures within a hermetically sealed annular space and/or to the wellbore casing emulating tubing.

In some implementations, the testing portion 104b can be configured with one or more heaters (not illustrated). The one or more heaters are capable of heating the annular space to wellbore-level temperatures.

Figure 2:
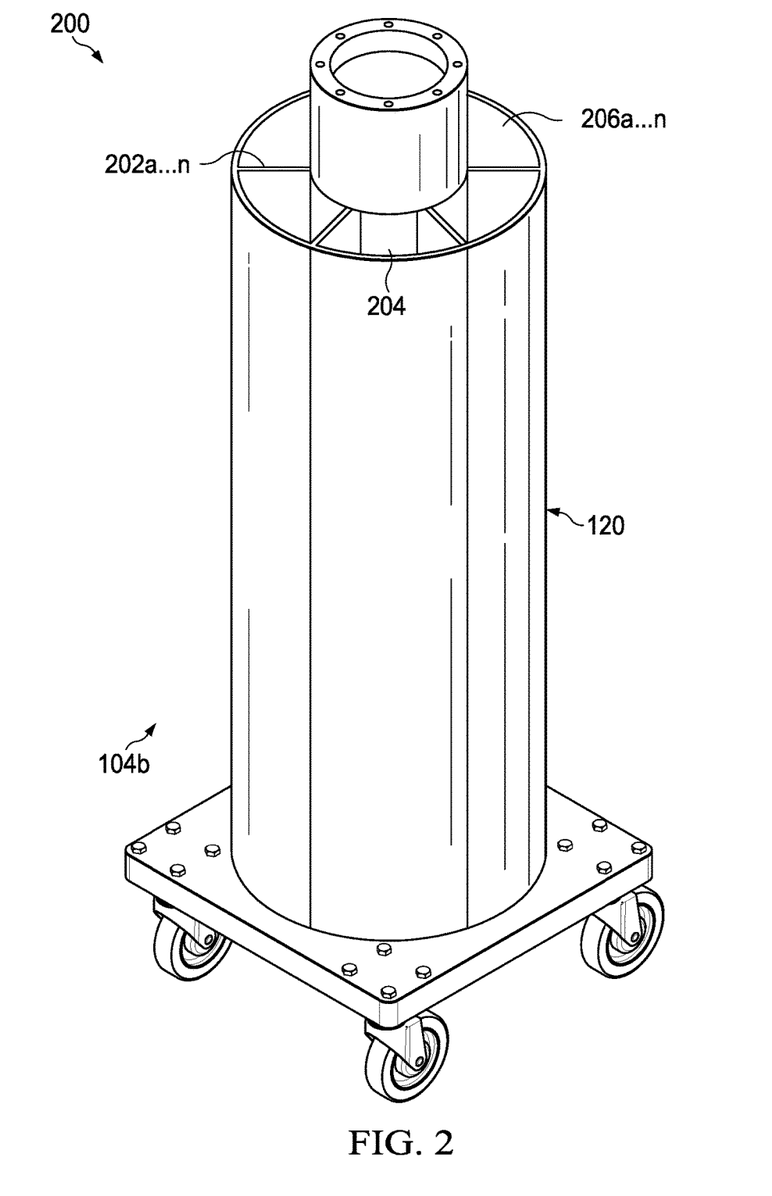
FIG. 2 is a perspective view of the testing portion of the test fixture of FIG. 1 according to an implementation.

FIG. 2 is a perspective view 200 of the testing portion 104b of test fixture 102 of FIG. 1 without an upper end module 118 according to an implementation. In some implementations, one or more dividing structures 202a . . . n are coupled to the outer surface of the wellbore casing emulating tubing 108 and to the inner surface of the outer tubing 120 in the axial direction to radially subdivide the annular space 204 into a plurality of sample sections 206a . . . n. For example, metallic plates can be welded to the outer surface of the wellbore casing emulating tubing 108 and to the inner surface of the outer tubing 120. Each sample section 206 can be used to place cement, cement-based, resin and/or other materials into the testing portion 104b of the test fixture 102. In some implementations, each dividing structure 202 provides a hermetic seal along the wellbore casing emulating tubing 108 and the inner surface of the outer tubing 120. In some implementations, the coupling of the bottom surface of the upper end module 118 to the upper edges of the outer tubing 120 and the upper edges of the one or more dividing structures 202a . . . n hermetically seals each individual sample section 206.

In some implementations, the previously described pump (not illustrated) is capable of producing individually configurable wellbore pressures within each hermetically sealed sample section 206. In some implementations, the previously described one or more heaters (not illustrated) are capable of heating each hermetically sealed sample section 206 to an individually configurable wellbore-level temperature.

In some implementations, the upper end module 118 of FIG. 1 comprises one or more sensors (not illustrated) to monitor conditions within each sample section 206 and/or one or more characteristics of the cement within each sample section 206. In some implementations, the outer tubing 120 and/or the internal bond-log tool receiving bore 110 can also be configured with sensors. Sensors can be, for example, for temperature, pressure, strain, and/or other data.

Figures 3A, 3B, 4:
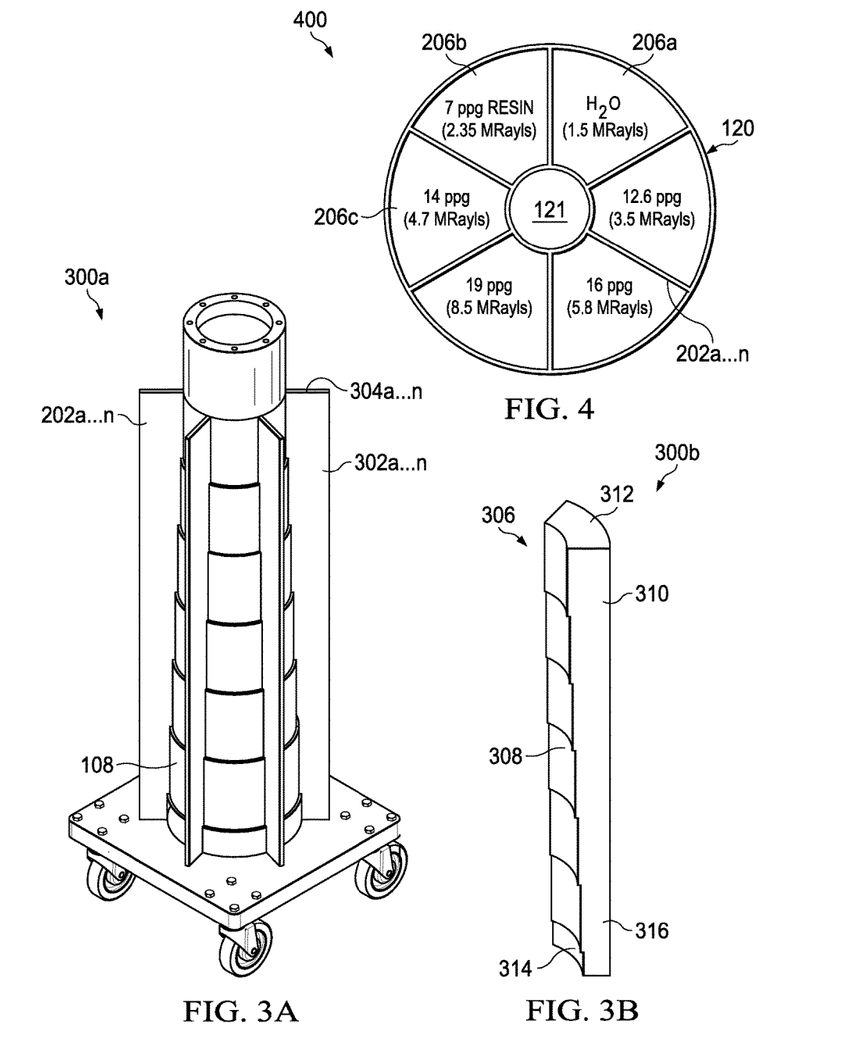
FIG. 3A is a perspective view of the testing portion of FIG. 2 with the outer tubing removed according to an implementation.
FIG. 3B is a perspective view of a hardened cement sample from a test fixture individual sample section according to an implementation.
FIG. 4 illustrates samples of cement having different acoustic impedances within fixture sample sections according to an implementation.

FIG. 3A is a perspective view 300a of the testing portion 104b with the outer tubing 120 removed according to an implementation. One or more dividing structures 202a . . . n are illustrated coupled to the outer surface of the wellbore casing emulating tubing 108 in the axial direction to radially subdivide the previously described annular space 204 into a plurality of sample sections 206a . . . n. The outer radial edges 302a . . . n of the one or more dividing structures 202a . . . n are coupled to the inner surface of the outer tubing 120. The upper edges 304a . . . n of each dividing structure 202a . . . n couple with the bottom surface of the upper end module 118.

In some implementations, radial step dimensions of the axially-stepped outer surface of the wellbore casing emulating tubing 108 can vary for each sample section. For example, in a sample section 206a, the axially-stepped outer surface can uniformly step in increasing thickness traveling axially downwards along the wellbore casing emulating tubing 108. In an adjacent sample section 206b, the axially-stepped outer surface can uniformly step in decreasing thickness traveling axially downwards along the wellbore casing emulating tubing 108. In some implementations, the wellbore casing emulating tubing 108 can radially be of a uniform thickness within an individual sample section 206.

FIG. 3B is a perspective view 300b of a hardened cement sample 306 from an individual test fixture sample section 206 according to an implementation. The illustrated hardened cement sample 306 has adopted a shape conforming to the dimensions of an individual sample section 206. For example, the inner surface 308 of the hardened cement sample 304 is shaped to conform to the axially-stepped outer surface of the wellbore casing emulating tubing 108 as illustrated in FIG. 3A (i.e., thicker at the top and thinner at the bottom). Likewise, the side, bottom, top, and rear surfaces, 310, 312, 314, and 316, respectively, of the hardened cement sample are consistent with the surfaces they rested against while hardening (e.g., here smooth, flat, and/or curved surfaces). Other surfaces, finishes, textures, and/or shapes, etc. for various components of the test fixture are considered to be within the scope of the disclosure. For example, the inner surface of the outer tubing 120 can be manufactured with a specified roughness to emulate a rough well formation. This roughness would affect the texture of the rear surface 316 of the hardened cement sample 306.

Moreover, cement bonds to the inner surface of the outer tubing 120 and the outer surface of the wellbore casing emulating tubing 108 which emulates casing and cementing operations in well applications. The bonding allows for optimum evaluation of multiple ABTs 106 under a wide range of media conformed by the different cement and casing systems.

FIG. 4 is an illustration 400 of samples of cement or other materials having different acoustic impedances within test fixture sample sections 206a . . . n according to an implementation. In some implementations, each sample section 206a . . . n comprises a different sample of cement and/or other material (e.g., resins, water, brine, drilling fluids, and/or other materials) formulated or used to produce a specified range of acoustic impedances. For example, the sample section 206a contains water with a known acoustic impedance of 1.6 MRayls, sample section 206b contains a 7 ppg (pounds per gallon) density resin with a known acoustic impedance of 2.35 MRayls, and sample section 206c contains a 14 ppg density cement at 4.7 MRayls. The different sample sections 204 allow the ABT 106 under test to be validated and/or calibrated against multiple materials of known densities and acoustic impedances. In some implementations the ABT 106 can measure the acoustic impedances of the different materials simultaneously. As acoustic impedance of a material is directly proportional to its density, the test fixture 102 allows an ABT 106 to be simultaneously validated and/or calibrated against a wide range of cement or other material densities/impedances encountered in well fields.

In some implementations, each sample section 206 must be acoustically uniform and stable, meaning, no major variation from top to bottom within the same sample of cement or other material. Likewise, no substantial density variations are acceptable within the same sample section 206.

Figure 5:
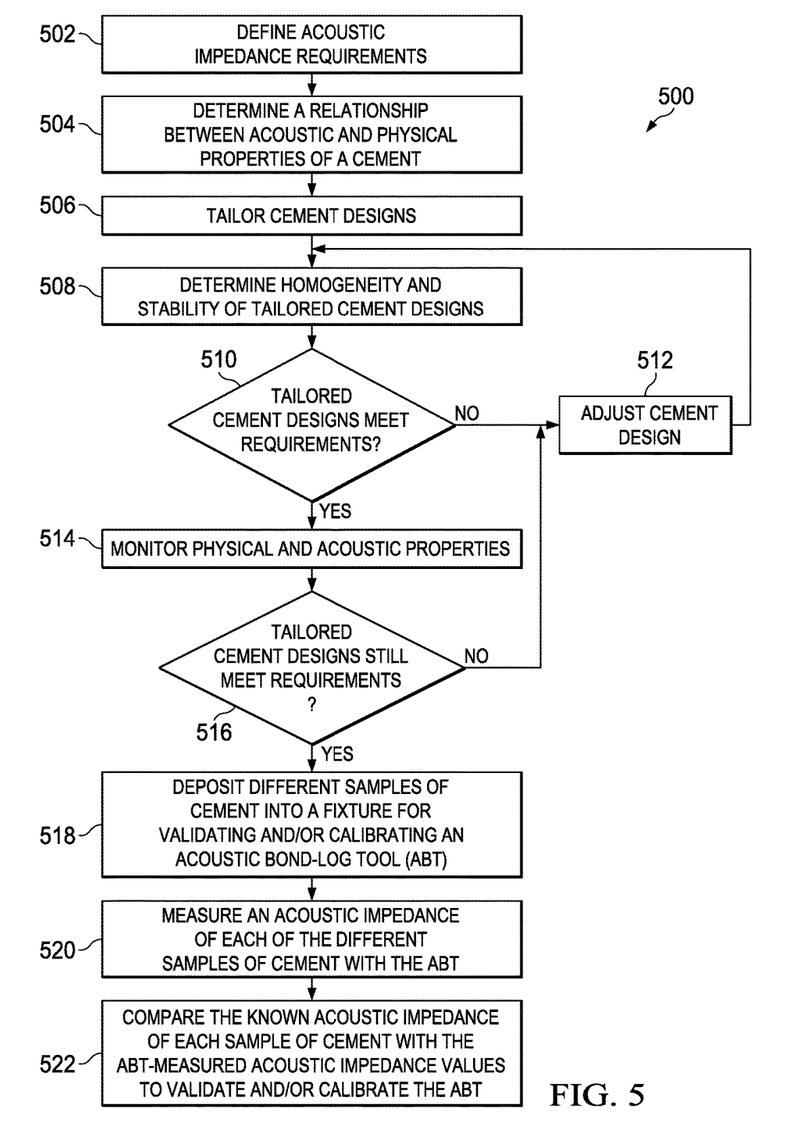
FIG. 5 is flow chart illustrating a method for validating an acoustic bond-log tool according to an implementation.

FIG. 5 is a flow chart illustrating a method 500 for validating an acoustic bond-log tool according to an implementation. For clarity of presentation, the description that follows generally describes method 500 in the context of FIGS. 1-2, 3A and 3B, and 4. In some implementations, various steps of method 500 can be run in parallel, in combination, in loops, or in any order.

At 502, acoustic impedance requirements are defined for cement to use for validating and/or calibrating an acoustic bond-log tool (ABT). From 502, method 500 proceeds to 504.

At 504, a relationship between acoustic and physical properties of a cement (e.g., acoustic impedance and density) is determined cement slurry density has been historically employed as one of the criteria used to classify well cements based upon cement application and/or an application environment to which the cement will be exposed (e.g. high-density slurries are employed for high strength requirements). Furthermore, velocity of sound wave propagation in cement depends on the density and elastic properties of the cement. This is reflected in the correlation shown below:

$$V_C = \sqrt{\frac{E}{\rho}}$$

Where Vc is the velocity of the compressional or longitudinal wave; E is the Young's modulus of the material or medium, and ρ is the density of the medium. Moreover, an acoustic variable can be defined as a material properly (acoustic impedance "Z" defined as the product of density of the material and its compressional velocity):

$$Z = V_C \rho$$

Multiple samples of cement representative of a broad range of cement slurry densities are evaluated in order to determine their acoustic impedance and establishing a correlation between the two variables. Here, only the material density is taken into disregarding all other characteristics (e.g., the influence of using different additives, water to cement ratio, and many other factors that may affect cement's properties). An approximately linear relationship exists between density and acoustic impedance, which facilitates the design of cement-based systems with specific acoustic properties. This allows for tailoring slurry designs to meet a specific acoustic impedance requirement. A calculation of acoustic impedance is performed for each cement sample. From 504, method 500 proceeds to 506.

At 506, cement designs are tailored based on results from 504. From 506, method 500 proceeds to 508.

At 508, homogeneity and stability of the tailored cement designs are determined. It is necessary to establish other parameters potential cement designs must fulfill in order to be considered a valid cement design for evaluation of the ABT. In some implementations, two main parameters are considered when designing validation cement slurries: 1) homogeneity/uniformity and 2) stability. Homogeneity/uniformity relates to the cement not segregating, settling, or possessing density variation among different sections of the cement (e.g., within a sample section). Stability relates to the cement's properties remaining consistent over time for testing purposes. An additional parameter that can be considered is mixability—indicating the flowability of the cement. From 508, method 500 proceeds to 510.

At 510, a determination is made as to whether the tailored cement designs meet necessary acoustic impedance requirements. If, at 510, a determination is made that the tailored cement designs meet necessary acoustic impedance requirements, method 500 proceeds to 514. If, at 510, a determination is made that the tailored cement designs do not meet necessary acoustic impedance requirements, method 500 proceeds to 512 where cement designs are adjusted.

At 514, physical and acoustic properties of the tailored cement designs are monitored. Typically, additional studies must be performed to determine the effect of other variables (e.g., time and degree of hydration) on both density and compressional velocity; and hence, acoustic impedance. While the density of cement based materials typically becomes stable after setting, the compressional velocity may continue to gradually change with further hydration of the cement, which can last for years in some instances. Therefore, the compressional velocity and density are monitored during extended periods of time in order to determine their effects on the acoustic impedance of the tailored cement. Taking these monitoring results into consideration, the tailored cement designs are further tailored. From 514, method 500 proceeds to 516.

At 516 a determination is made as to whether the tailored cement designs still meet necessary acoustic impedance requirements. If at 516, a determination is made that the tailored cement designs still meet necessary acoustic impedance requirements, method 500 proceeds to 518. If, at 516, a determination is made that the tailored cement designs still do not meet necessary acoustic impedance requirements, method 500 proceeds to 512 where cement designs are adjusted.

At 518, different samples of cement having a range of known acoustic impedances are deposited into a test fixture for validating the ABT. In some implementations, other materials, such as water, resin, and the like can be deposited into the test fixture to provide known data points. From 518, method 500 proceeds to 520.

At 520, an acoustic impedance of each of the different samples of cement is measured with the ABT. In some implementations, each sample of cement can be placed under different pressure and temperature conditions similar to well-bore conditions. From 520, method 500 proceeds to 522.

At 522, the known acoustic impedance of each sample of cement compared with the measured acoustic impedance in order to validate and/or calibrate the ABT. After 522, method 500 stops.

The foregoing description is provided in the context of one or more particular implementations. Various modifications, alterations, and permutations of the disclosed implementations can be made. Thus, the present disclosure is not intended to be limited only to the described and/or illustrated implementations, but is to be accorded the widest scope consistent with the principles and features disclosed herein.

What is claimed is:

1. A method for validating an acoustic bond-log tool, comprising:
   having a test fixture, comprising:
   a wellbore casing emulating tubing with a bond-log tool receiving bore;
   an outer tubing forming a perimeter of an annulus surrounding the wellbore casing emulating tubing and emulating a well formation; and
   a dividing structure coupled in the axial direction to the outer surface of the wellbore casing emulating tubing and to the inner surface of the outer tubing to radially subdivide the annulus into a plurality of sample sections, each sample section containing a sample of a material having a known acoustic impedance; and
   validating the acoustic bond-log tool by comparing a bond-log tool measurement of the acoustic impedance of each sample in a particular sample section to the known acoustic impedance of the sample.

2. The method of claim 1, further comprising coupling an upper end module to the upper edges of the plurality of sample sections, wherein the upper end module surrounds the wellbore casing emulating tubing to hermetically seal each sample section.

3. The method of claim 2, wherein the upper end module comprises one or more sensors.

4. The method of claim 2, further comprising:
   configuring a port to provide access to a sealed sample section;
   coupling a pump to the port, the pump capable of producing wellbore pressures within the sealed sample section; and
   associating a heater with the fixture, the heater capable of heating the sealed sample section.

5. The method of claim 2, further comprising:
   coupling a wellbore tubing upper end module to upper edges of the wellbore casing emulating tubing to seal the wellbore casing emulating tubing;
   configuring a port to provide access to the sealed wellbore casing emulating tubing; and
   coupling a pump to the port, the pump capable of producing wellbore pressures within the sealed wellbore casing emulating tubing.

6. The method of claim 4, wherein the pump and heater can produce a pressure and temperature for the sealed sample section independently of a pressure and temperature associated with another sealed sample section.

7. The method of claim 1, wherein each sample section comprises a different sample of a material formulated to produce a specified range of acoustic impedances, the material in each sample section having a different acoustic impedance.

8. The method of claim 1, wherein the material formulated to produce a specified range of acoustic impedances includes at least one of resin, water, brine, or drilling fluid.

9. The method of claim 1, further comprising configuring the wellbore casing emulating tubing with a stepped outer surface to emulate different wellbore casing sidewall thicknesses.

10. The method of claim 9, wherein the dimensions of the stepped outer surface of the wellbore casing emulating tubing can vary for each sample section.

11. The method of claim 1, wherein one or more of the sample sections comprises a sensor.

12. The method of claim 1, further comprising configuring the bond-log tool receiving bore to be hermetically sealed.

13. An acoustic bond-log tool validation method, comprising:
   having a plurality of sample sections surrounding a wellbore casing emulating tubing, the plurality of sample sections forming a radially divided annulus around the wellbore casing emulating tubing, each of the plurality of sample sections holding a different sample of a material formulated to produce a specified range of acoustic impedances;
   measuring, within each sample section, an acoustic impedance of each of the different samples with the acoustic bond-log tool; and
   comparing the known acoustic impedance of each sample with the measured acoustic impedance to validate the acoustic bond-log tool.

14. The method of claim 13, further comprising coupling an upper end module to the upper edges of the plurality of sample sections, wherein the upper end module surrounds the casing emulating tubing to hermetically seal each sample section.

15. The method of claim 14, further comprising:
coupling a pump to a port providing access to a sealed sample section, the pump operable to produce wellbore pressures within the sealed sample section; and
associating a heater with the fixture, the heater operable to heat the sealed sample section.

16. The method of claim 14, further comprising:
coupling a wellbore tubing upper end module to upper edges of the wellbore casing emulating tubing to seal the wellbore casing emulating tubing; and
coupling a pump to a port providing access to the sealed wellbore casing emulating tubing, the pump operable to produce wellbore pressures within the sealed wellbore casing emulating tubing.

17. The method of claim 15, wherein the pump and heater produce a pressure and temperature for the sealed sample section independent of a pressure and temperature associated with another sealed sample section.

18. A method for validating an acoustic bond-log tool, comprising:
containing different samples of a material in each of a plurality of sample sections surrounding an emulated well-bore casing of a test fixture, each sample formulated to produce a different known acoustic impedance;
measuring an acoustic impedance of each of the different samples within each sample section with the bond-log tool; and
comparing the known acoustic impedance of each sample with the measured acoustic impedance to validate the acoustic bond-log tool.

19. The method of claim 18, wherein the test fixture is divided into the plurality of sample sections, each sample section containing different ones of the samples with the different acoustic impedance.

20. The method of claim 19, further comprising producing a pressure and temperature for each sample section.

21. The method of claim 20, wherein the produced pressure and temperature is different for each sample section.

22. The method of claim 18, further comprising measuring the acoustic impedances of the different samples simultaneously.

23. The method of claim 18, measuring the acoustic impedance of each sample through different wall thicknesses of the emulated well-bore casing.

* * * * *

UNITED STATES PATENT AND TRADEMARK OFFICE
CERTIFICATE OF CORRECTION

PATENT NO. : 10,241,086 B2
APPLICATION NO. : 15/028761
DATED : March 26, 2019
INVENTOR(S) : Walmy Cuello Jimenez et al.

It is certified that error appears in the above-identified patent and that said Letters Patent is hereby corrected as shown below:

In the Specification

In Column 2, Line 9, after --cement evaluation-- delete "its" and insert --in--

In Column 3, Line 21, after --configured with-- delete "art" and insert --an--

In Column 5, Line 11, delete "sample 304" and insert --sample 306--

In Column 5, Line 45, after --sample sections-- delete "204" and insert --206--

In Column 6, Line 25, after --material-- delete "properly" and insert --property--

In Column 7, Line 38, delete "cement compared" and insert --cement is compared--

Signed and Sealed this
Eighteenth Day of June, 2019

Andrei Iancu
*Director of the United States Patent and Trademark Office*